(12) United States Patent
Datta et al.

(10) Patent No.: US 9,528,130 B2
(45) Date of Patent: Dec. 27, 2016

(54) PROCESSES AND CONTROL SYSTEMS FOR HIGH EFFICIENCY ANAEROBIC CONVERSION OF HYDROGEN AND CARBON OXIDES TO ALCOHOLS

(71) Applicants: Rathin Datta, Chicago, IL (US); Steven G. Calderone, Chicago, IL (US); Jianxin Du, Naperville, IL (US); Robert Hickey, Okemos, MI (US); Richard E. Tobey, St. Charles, IL (US)

(72) Inventors: Rathin Datta, Chicago, IL (US); Steven G. Calderone, Chicago, IL (US); Jianxin Du, Naperville, IL (US); Robert Hickey, Okemos, MI (US); Richard E. Tobey, St. Charles, IL (US)

(73) Assignee: Synata Bio, Inc., Warrenville, IL (US)

( * ) Notice: Subject to any disclaimer, the term of this patent is extended or adjusted under 35 U.S.C. 154(b) by 67 days.

(21) Appl. No.: 14/175,928

(22) Filed: Feb. 7, 2014

(65) Prior Publication Data

US 2014/0227752 A1    Aug. 14, 2014

Related U.S. Application Data

(60) Provisional application No. 61/762,702, filed on Feb. 8, 2013.

(51) Int. Cl.
  *C12P 7/16* (2006.01)
  *C12P 7/06* (2006.01)
  *C12P 7/04* (2006.01)

(52) U.S. Cl.
  CPC .. *C12P 7/16* (2013.01); *C12P 7/04* (2013.01); *C12P 7/06* (2013.01); *Y02E 50/10* (2013.01); *Y02E 50/17* (2013.01)

(58) Field of Classification Search
  None
  See application file for complete search history.

(56) References Cited

FOREIGN PATENT DOCUMENTS

NZ    WO2011/139163    *  11/2011    ............... C12P 7/06

* cited by examiner

*Primary Examiner* — Karen Cochrane Carlson
*Assistant Examiner* — Jennifer M. H. Tichy
(74) *Attorney, Agent, or Firm* — Cardinal Law Group

(57) ABSTRACT

High conversion efficiency processes are disclosed for the anaerobic bioconversion of syngas to alcohol. The processes use bioreactors that have a non-uniform gas composition and a substantially uniform liquid composition such as deep tank bioreactors. By maintaining certain electron to carbon mole ratios in the syngas feed to the bioreactors and certain partial pressures of carbon dioxide in the off gas from the bioreactors, at least about 80 percent of the hydrogen and at least about 95 percent of the carbon monoxide in the feed can be consumed.

17 Claims, 1 Drawing Sheet

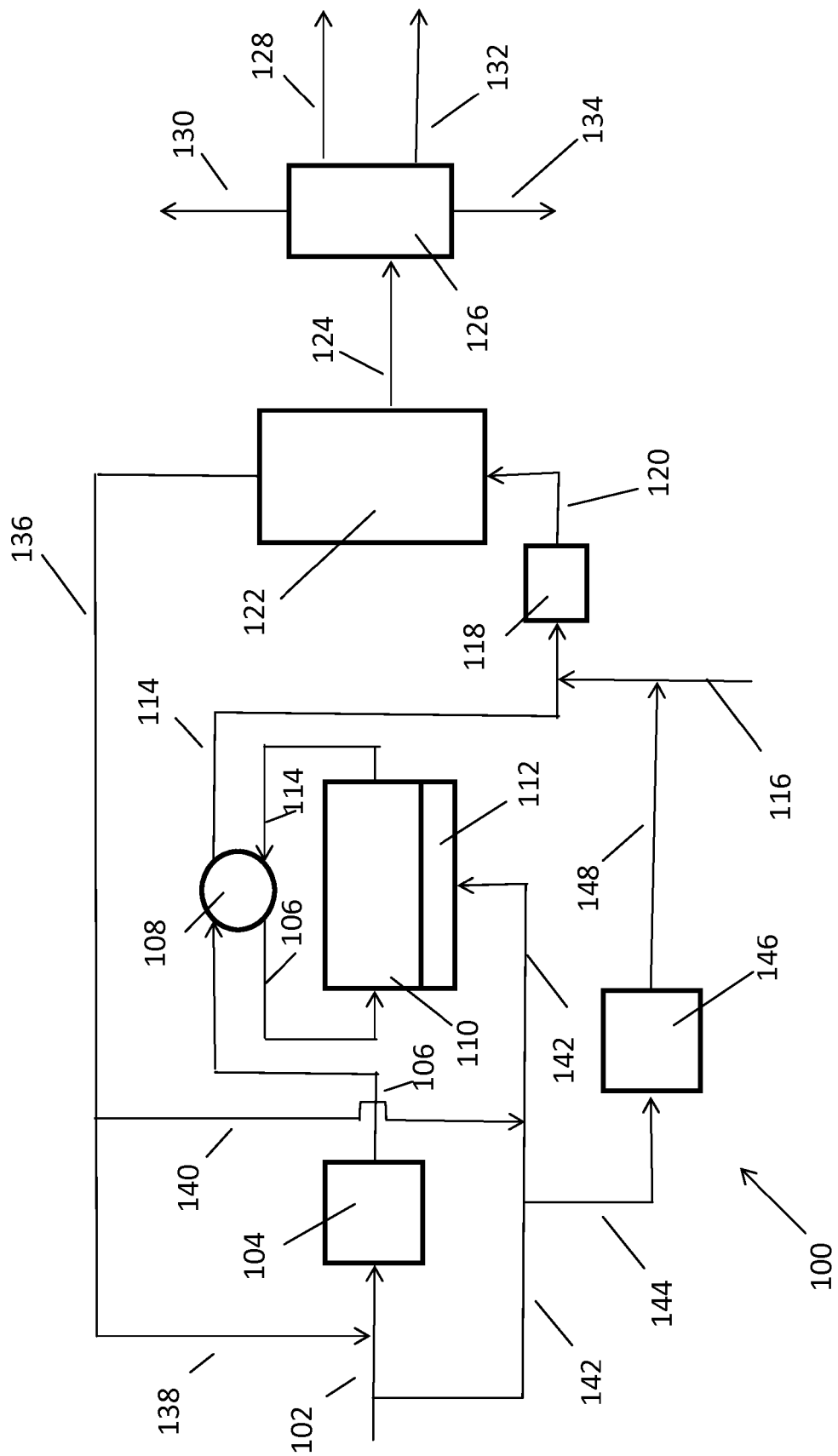

PROCESSES AND CONTROL SYSTEMS FOR HIGH EFFICIENCY ANAEROBIC CONVERSION OF HYDROGEN AND CARBON OXIDES TO ALCOHOLS

CROSS REFERENCE TO RELATED APPLICATIONS

Priority is claimed to U.S. provisional application Ser. No. 61/762,702, filed on Feb. 8, 2013.

FIELD OF THE INVENTION

This invention pertains to processes and control systems for anaerobic conversion of hydrogen and carbon oxides to alcohols especially ethanol, propanol and butanol.

BACKGROUND

Anaerobic fermentations of hydrogen and carbon monoxide involve the contact of the substrate gas in an aqueous fermentation menstruum with microorganisms capable of generating alcohols such as ethanol, propanol, i-butanol and n-butanol. The production of these alcohols requires significant amounts of hydrogen and carbon monoxide. For instance, the theoretical equations for the conversion of carbon monoxide and hydrogen to ethanol are:

$$6CO + 3H_2O \cdot C_2H_5OH + 4CO_2$$

$$6H_2 + 2CO_2 \cdot C_2H_5OH + 3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, from partial oxidation or reforming of natural gas and/or biogas from anaerobic digestion or landfill gas or off-gas streams of various industrial methods such as off gas from coal coking and steel manufacture. The substrate gas contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

These substrate gases are typically more expensive than equivalent heat content amounts of fossil fuels. Hence, a desire exists to use these gases efficiently to make higher value products. The financial viability of any conversion process, especially to commodity chemicals such as ethanol, will depend, in part, upon the costs of the feedstocks, conversion efficiency and operating and capital costs for generating the substrate gases; and upon the capital costs, the efficiency of conversion of the carbon monoxide and hydrogen to the sought products and the energy costs to effect the conversion of the substrate gases to the higher value products.

In a bioreactor, hydrogen and carbon oxides pass from the gas phase to being dissolved in the aqueous menstruum, and then the dissolved hydrogen and carbon oxides contact the microorganisms for bioconversion. Due to the low solubilities of carbon monoxide and, especially, hydrogen in aqueous media, mass transfer can be a limiting factor rate and conversion in the bioconversion to alcohol. Therefore challenges exist in the design of commercial scale bioreactors that provide for the sought mass transfer while still enabling a high conversion of gas substrate at capital and operating costs that enable such a facility to be commercially competitive.

From the standpoint of low capital and energy consumption, deep tank bioreactors have been proposed to provide longer contact times between the substrate gases and the aqueous fermentation menstruum with the objective of obtaining higher conversions of the substrate gases to the higher value products. In deep tank bioreactors, the height of the aqueous menstruum is a significant determinant of the contact time for the mass transfer and bioconversion to occur. On a commercial scale, deep tank bioreactors have a depth of at least about 10, preferably at least about 15, meters.

One type of deep tank bioreactor is a stirred tank bioreactor which uses a motor driven impeller to provide liquid flow in the bioreactor and distribute the gases in the aqueous menstruum. The stirring may also facilitate increasing the contact time between the gases and the aqueous menstruum. Due to the scale, low stirring rates are typically used in deep tank bioreactors. Another type of deep tank bioreactor is a bubble column bioreactor wherein the substrate gases are introduced at the bottom of the vessel and bubble through the aqueous menstruum. Advantageously, commercial-scale bubble column bioreactors are relatively simple in design and construction and require relatively little energy to operate. Achieving liquid mixing in a deep tank bubble column can be problematic. Mechanically pumping aqueous menstruum may facilitate liquid flow. As discussed herein, the use of smaller bubbles may form lower density dispersions that facilitate mixing. Moreover, smaller bubbles favor the mass transfer of hydrogen and carbon oxides from the gas to liquid phase. A third type of deep tank bioreactor uses one or more, gas-lift riser sections to facilitate liquid flow and mixing. Typically, gas is introduced at the bottom of a riser section and due to a lower density, the aqueous menstruum flows upwardly. At the top of the riser section, the liquid phase passes to a down flow section for return to the bottom of the riser section.

The off gases from bioreactors contain substrate that was not bioconverted and diluents such as methane and nitrogen. Although off gases can be recycled to the bioreactor or passed to another bioreactor, challenges can exist. For instance, the substrate gases may contain diluents that if recycled to a bioreactor, can build-up and reduce the partial pressure, and thus driving forces for mass transfer of hydrogen and carbon monoxide to the aqueous menstruum. Moreover, the off gas from a deep tank bioreactor would need to be compressed for recycle or for passage to a sequential bioreactor. A sequential bioreactor represents additional capital and operating costs, and since the concentration of hydrogen and carbon monoxide in the off gas from the first reactor is reduced due to the anaerobic bioconversion, the incremental conversion efficiencies achieved may not be economically justifiable.

Bell in United States published patent application No. 20100105118 discloses an integrated process for making alcohols which is said to provide high bioconversions of carbon monoxide in fermentations in the absence of oxygen. Bell notes at paragraph 0013 that in theory, carbon dioxide may be used as a reactant for the production of higher alcohols such as ethanol. However, he states that in practice the fermentation route to higher alcohols tends to be a net producer of carbon dioxide. In his disclosed process, the gas from the bioreactor which contains carbon dioxide is fed to a steam reformer. The reformer is either operated dry or with a mole ratio of water to carbon dioxide of less than 5:1. Bell states in paragraph 0025:

" . . . the integrated process of the present invention operates with a hydrogen excess and efficiently converts the carbon dioxide in the feed to the reforming process to carbon monoxide, and actually results in a lower process inventory of carbon dioxide."

Bell confirms the carbon dioxide net make of his process and the low conversion of hydrogen in the examples. In Example 1, 107 kmoles per hour of carbon dioxide are fed to the bioreactor and 194 kmoles of carbon dioxide are contained in the off gas from the bioreactor. Hydrogen is fed to the bioreactor at a rate of 318 kmoles per hour, and 231 kmoles per hour of hydrogen are contained in the off gas for a hydrogen conversion of about 28 percent. Similarly in Example 2, the feed to the bioreactor contains 25 kmole per hour of carbon dioxide, and 117 kmole per hour of carbon dioxide is contained in the off gas. Hydrogen is fed to the bioreactor at a rate of 298 kmole per hour with 206 kmole per hour of hydrogen passing to the off gas for a hydrogen conversion of about 31 percent. Bell subjects the off gas to membrane separation unit operation to remove hydrogen to reduce the amount of hydrogen being passed back to the reformer. This hydrogen is fed to the hot box of the reformer as a portion of the fuel. See paragraph 0075.

Although Bell may have reduced carbon dioxide emissions as compared to the use of autothermal reforming or traditional steam reforming, the low conversion of hydrogen detracts from the commercial viability of the disclosed process.

Processes are therefore sought that can provide very high conversions of both hydrogen and carbon monoxide in commercial-scale, continuous operations to alcohols. Desirably such processes can be deployed in commercial-scale, deep tank bioreactors.

SUMMARY

By this invention continuous processes and control systems are provided for the anaerobic conversion of hydrogen and carbon oxides to higher alcohols, especially ethanol, propanol and butanol, that enable high conversions to be achieved. The bioreactors are characterized as having a substantially uniform aqueous menstruum composition and a substantially non-uniform substrate composition, i.e., the rate of gas transfer to the liquid phase exceeds the rate of mixing in the liquid phase. This non-uniformity of substrate composition exists in deep tank bioreactors. Thus, the poor distributions of deep tank bioreactors, as compared to continuous stirred tank bioreactors, can be used to advantage.

In the processes of this invention, a net bioconversion of carbon dioxide occurs in contrast to the processes disclosed by Bell. Moreover, the processes of this invention are able to obtain a high conversion of valuable hydrogen to alcohols. The processes of this invention additionally use gas substrate having certain electron to carbon relationships and maintain certain partial pressures of carbon dioxide in the off gases from the bioreactor to obtain a high conversion of hydrogen.

In one broad aspect this invention pertains to continuous processes for the anaerobic bioconversion of a gas substrate comprising carbon monoxide, hydrogen and carbon dioxide in an aqueous menstruum containing microorganisms suitable for converting said substrate to alcohol comprising:

a. continuously introducing said substrate in the form of gas bubbles at one or more gas inlets of a bioreactor assembly having at least one bioreactor for containing said menstruum, said bioreactor having at least one gas inlet and at least one gas outlet and at least one bioreactor in the bioreactor assembly is characterized as having a substantially uniform aqueous menstruum and a substantially non-uniform substrate composition between the gas inlet portion and the gas outlet portion wherein the cumulative substrate introduced into the bioreactor assembly through said one or more gas inlets has a ratio of electrons to carbon atoms in the range of about 5.2:1 to 6.8:1, preferably between about 5.5:1 to 6.5:1, and most preferably between about 5.5:1 or 5.7:1 to 6.4:1;

b. maintaining contact between the gas bubbles and said menstruum to provide an alcohol-containing menstruum and a substrate depleted gas phase at a gas outlet of said bioreactor assembly, said duration of contact being sufficient to convert at least about 80 or 85, preferably at least about 90, percent of the hydrogen and at least about 95, often at least about 98, preferably at least about 99, percent of the carbon monoxide in the gas substrate to alcohol;

c. continuously withdrawing substrate depleted gas phase from said bioreactor assembly at said at least one gas outlet wherein the substrate depleted gas phase being withdrawn from the bioreactor assembly has a partial pressure of carbon dioxide in the range of about 2.5 and 20 or 25, preferably between about 2.5 or 3.5 and 10, kPa; and d. continuously or intermittently withdrawing a portion of said menstruum from said bioreactor assembly for recovery of said alcohol, said withdrawal being sufficient to maintain the alcohol in said menstruum below a concentration that unduly adversely affects the microorganisms.

Where substrate is provided to the bioreactor assembly via more than one gas inlets, the composition of the substrate feed may be the same or different at each gas inlet provided that the overall, or cumulative gas substrate introduced into the bioreactor assembly has an electron to carbon atom ratio in accordance with this invention. Overall or cumulative gas substrate means the total exogenous gas substrate introduced to the bioreactor assembly through all gas inlets of the bioreactors. For instance, if more than one bioreactor is used, a portion of the substrate, which may have the same or different composition as that fed to the prior bioreactor, may be added to the off gas from one stage and the combined gases passed to the subsequent stage. It is also possible to add a portion of the substrate at different locations in the height of the bioreactor. Especially with a deep tank bioreactor, a benefit can be realized in reducing compression costs. However, the location of the introduction of such portion of the substrate should preferably not unduly impede the progress of the bioconversion due to regions of low concentrations of substrate occurring in the bioreactor.

In another broad aspect of this invention, processes are provided for controlling the operation of a bioreactor assembly for the anaerobic bioconversion of a gas substrate comprising carbon monoxide, hydrogen and carbon dioxide in an aqueous menstruum containing microorganisms suitable for converting said substrate to alcohol wherein:

a. said substrate is continuously introduced in the form of gas bubbles at one or more gas inlets of a bioreactor assembly having at least one bioreactor for containing said menstruum, said bioreactor having at least one gas inlet and at least one gas outlet in which at least one bioreactor is characterized as having a substantially uniform aqueous menstruum and a substantially non-uniform substrate concentration between the gas inlet and the gas outlet;

b. contact is maintained between the gas bubbles and said menstruum to provide an alcohol-containing menstruum and a substrate depleted gas phase at a gas outlet of said bioreactor assembly;

c. substrate depleted gas phase is continuously withdrawn from said bioreactor assembly at the at least one gas outlet; and d. a portion of said menstruum is continuously or intermittently withdrawn from said bioreactor assembly for recovery of said alcohol, said withdrawal being sufficient to maintain the alcohol in said menstruum below a concentration that unduly adversely affects the microorganisms, with the process further comprising adjusting the ratio of electrons to carbon atoms gas bubbles at said gas inlet portion to be within in the range of about 5.2:1 to 6.8:1, preferably between about 5.5:1 to 6.5:1, and most preferably between about 5.5:1 to 6.4:1 and adjusting the carbon dioxide concentration in the gas substrate to provide a partial pressure of carbon dioxide in the substrate depleted gas phase at the at least one gas outlet to be in the range of about 2.5 and 20 or 25, preferably between about 2.5 or 3.5 and 10, kPa.

The gas substrate may be obtained in any convenient manner. Usually the gas substrate comprises a syngas from the gasification, partial oxidation or reforming of a carbonaceous feedstock, and most preferably from steam reforming as a high hydrogen to carbon oxides ratio is contained in the reformate. In some instances, especially where using a steam reformer or oxygen fed autothermal reformer, the gas substrate being introduced into the bioreactor assembly comprises at least about 80, more preferably at least about 90, mole percent of carbon monoxide, hydrogen and carbon dioxide. With an air fed autothermal reformer, the nitrogen content of the gas substrate is usually in the range of about 25 to 30 volume percent.

In accordance with the processes and control systems of this invention, the electron to carbon ratio is adjusted to fall within a specified range, and the carbon dioxide in the gas substrate is controlled such that the substrate depleted gas phase, or off gas, from the bioreactor assembly is maintained in a specified range of partial pressures. By operating at the electron to carbon ratios of this invention, it is possible to adjust the partial pressure of carbon dioxide in the substrate depleted gas to fall within the recited ranges where sufficient carbon dioxide is retained in the aqueous menstruum to promote conversion of hydrogen to alcohol but without unduly adversely affecting the mass transfer of hydrogen and carbon monoxide to the aqueous menstruum. In some instances it may be necessary to adjust the composition syngas to provide the sought composition for the overall gas substrate. The adjustment may occur prior to introducing the gas substrate into the bioreactor assembly or by introducing a gas substrate of a different composition into the bioreactor assembly at a different gas inlet as described above. The adjustment, especially where the gas substrate is carbon deficient such as syngas from a steam reformer, can be accomplished by adding carbon dioxide to the gas substrate. Where the gas is electron deficient, a gas richer in hydrogen or carbon monoxide may be added to the gas substrate to accomplish the adjustment, e.g., a coke oven gas.

Adjustment may also be effected, especially where syngas for the gas substrate is obtained from autothermal reforming by controlling the conditions of preheat temperature, oxygen supply, and steam ratio, to provide an overall, or cumulative, gas substrate for introducing into the bioreactor assembly that possesses a desired electron to carbon ratio. Preferably where the syngas for the gas substrate is obtained from steam reforming, the electron to carbon ratio of the cumulative gas substrate fed to the bioreactor assembly is in the range of 5.7:1 or 5.8:1 to 6.3:1 or 6.4:1. Where the syngas for the gas substrate is obtained from autothermal reforming, the electron to carbon ratio of the cumulative gas substrate fed to the bioreactor assembly is preferably in the range of 5.5:1 or 5.6:1 to 5.8:1 or 6.0:1.

The preferred processes of this invention use a deep tank bioreactor, most preferably a deep tank bubble column bioreactor using small bubbles to promote liquid mixing. Although the bioreactor assembly can comprise two or more bioreactors in gas flow series, from a capital and operating cost standpoint, only one bioreactor stage can often be employed while still obtaining the high conversion of hydrogen and carbon monoxide. Advantageously, the electron to carbon ratios of the gas substrate to the bioreactor assembly result in a sufficiently low concentration of carbon monoxide in the gas substrate that carbon monoxide inhibition is not a factor in the operation of a bubble column bioreactor of the depth required to provide the sought conversions.

The preferred processes of this invention exhibit a high conversion efficiency of carbon to alcohol. On a total carbonaceous feedstock, including feedstock used to provide heat energy to the process for generating the syngas, the conversion efficiency is often at least about 50, preferably at least about 60, and sometimes at least about 63 or 65, atomic percent of the feedstock introduced is converted to alcohol.

In another broad aspect this invention pertains to continuous processes for the anaerobic bioconversion of a syngas comprising carbon monoxide, hydrogen, carbon dioxide and nitrogen in an aqueous menstruum containing microorganisms suitable for converting said substrate to alcohol comprising:

a. continuously reforming a hydrocarbonaceous feedstock by autothermal reforming using air as the source of oxygen for the autothermal reforming, said autothermal reforming being operated to provide a syngas having an electron to carbon atom ratio of between about 5.5:1 and 6.0:1, preferably between about 5.6:1 to 5.8:1, and a nitrogen concentration of between about 25 and 35 mole percent;

b. continuously introducing said syngas in the form of gas bubbles at one or more gas inlets of a bioreactor assembly having at least one bioreactor for containing said menstruum, said bioreactor having at least one gas inlet and at least one gas outlet and at least one bioreactor in the bioreactor assembly is characterized as having a substantially uniform aqueous menstruum and a substantially non-uniform substrate concentration between the gas inlet and the gas outlet;

b. maintaining contact between the gas bubbles and said menstruum to provide an alcohol-containing menstruum and a syngas depleted gas phase at a gas outlet of said bioreactor assembly, said duration of contact being sufficient to convert at least about 90 percent of the hydrogen and at least about 95 or 98, preferably at least about 99, percent of the carbon monoxide in the gas substrate to alcohol;

c. continuously withdrawing syngas depleted gas phase from said bioreactor assembly at said at least one gas outlet wherein the syngas depleted gas phase being withdrawn from the bioreactor assembly has a partial pressure of carbon dioxide in the range of about 2.5 and 25, preferably between about 2.5 or 3.5 and 10, kPa; and d. continuously or intermittently withdrawing a portion of said menstruum from said bioreactor assembly for recovery of said alcohol, said withdrawal being sufficient to maintain the alcohol in said menstruum below a concentration that unduly adversely affects the microorganisms.

Typically air is not used as the oxygen source for autothermal reforming due to the substantial amount of nitrogen that would be contained in the produced syngas. The production of oxygen, however, requires significant capital and operating expense and thus often makes autothermal reforming less preferred than steam reforming of a hydrocarbonaceous feedstock which uses no oxygen to produce a syngas. By this invention it has been found that high feedstock conversion efficiencies can be achieved even though the syngas contains a significant mole fraction of nitrogen which reduces the partial pressure of hydrogen and carbon monoxide. An important criterion to enable the use of air as the oxygen source is the maintenance of an electron to carbon atom ratio syngas in the range set forth above, adequate mass transfer to the aqueous menstruum can occur to obtain the high hydrogen conversions. Moreover, as the partial pressure of carbon dioxide of the syngas depleted gas phase is maintained between about 2.5 and 20 or 25 kPa both the rate of bioconversion of hydrogen to ethanol and the driving force for mass transfer of hydrogen from the gas to aqueous phase operate together to achieve the high conversion of hydrogen. Thus, with the high conversion of hydrogen and carbon monoxide, the residual energy in the syngas depleted gas phase is at a level where capture of that energy is not essential to provide a high efficiency of conversion of feedstock to alcohol.

BRIEF DESCRIPTION OF THE DRAWINGS

FIG. 1 is a schematic depiction of an apparatus suitable for practicing the processes of this invention.

DETAILED DISCUSSION

Definitions

Alcohol means one or more alkanols containing two to six carbon atoms. In some instances alcohol is a mixture of alkanols produced by the microorganisms contained in the aqueous menstruum.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

The term Component Composition means the composition of a gas where both water and nitrogen have been excluded from the calculation of the concentration of the components. As used herein, unless otherwise stated, compositions of gases are on an anhydrous basis and exclude the presence of nitrogen.

Electron to carbon ratio is calculated as the quotient of the quantity of two times the sum of the concentrations of carbon monoxide and hydrogen divided by quantity of the sum of the concentrations of carbon monoxide and carbon dioxide:

$$e^-/C=2([CO]+[H_2])/([CO]+[CO_2]).$$

The abbreviation ppm means parts per million. Unless otherwise stated or clear from the context, ppm is on a mole basis (ppm (mole)).

Carbon monoxide inhibition means that microorganisms are adversely affected by a high concentration of dissolved carbon monoxide in the aqueous menstruum resulting in a significantly reduced, e.g., reduced by at least 15 percent, conversion of carbon monoxide or hydrogen per gram of active cells per liter, all other conditions remaining the same. An inhibitory concentration of dissolved carbon monoxide means that a higher conversion of carbon monoxide or hydrogen per gram of active cells per liter occurs at a lower dissolved concentration of carbon monoxide. The inhibitory effect may occur in a localized region in the aqueous menstruum; however, the occurrence of a carbon monoxide inhibition is typically observed by assessing the specific activity rate, i.e., the mass bioconsumed per mass of active microorganism per unit time, which under steady-state conditions can be approximated by the overall conversion for the volume of aqueous menstruum in the bioreactor. The concentration of carbon monoxide dissolved in the aqueous menstruum that results in carbon monoxide inhibition varies depending upon the strain of microorganism and the fermentation conditions.

Aqueous menstruum, or aqueous fermentation menstruum, means a liquid water phase which may contain dissolved compounds including, but not limited to hydrogen, carbon monoxide, and carbon dioxide.

Intermittently means from time to time and may be at regular or irregular time intervals.

A concentration of alcohol below that which unduly adversely affects the rate of growth of the culture of microorganisms will depend upon the type of microorganism and the alcohol. An unduly adverse effect on the growth rate means that a significant, usually at least a 20 percent, decrease in the growth rate of the microorganisms is observed in comparison to the growth rate observed in an aqueous menstruum having about 10 grams per liter alcohol therein, all other parameters being substantially the same.

Substantial uniformity in liquid phase means that the alcohol concentration in the liquid phase is substantially the same throughout a bioreactor. Usually the concentration of the alcohol is within about 0.2 mole percentage points in a uniform liquid phase.

Substantial non-uniformity of substrate means that the concentration (both in the gas bubbles and dissolved) of at least one component provided by the gas substrate changes by at least 50 percent between the point of entry of the gas into a bioreactor and the point that the gas emerges from the aqueous fermentation menstruum.

Deep tank bioreactor is a bioreactor having a depth of at least about 10 meters and can be operated to provide a substantial non-uniform substrate composition over the depth of the aqueous menstruum contained in the bioreactor. The term bubble column bioreactor as used herein refers to a deep tank bubble column bioreactor unless otherwise explicitly stated and include deep tank reactors where the gas is introduced as small bubbles to promote mixing. A commercial scale bioreactor has a capacity for aqueous menstruum of at least 1 million, and more preferably at least about 5, say, about 5 to 25 million, liters.

Stable gas-in-liquid dispersion means a mixture of gas bubbles in liquid where the bubbles predominantly flow in the same direction as the liquid currents in the bioreactor and may cause currents in the bioreactor, and the dispersion is sufficiently stable that it exists throughout the aqueous menstruum.

Syngas means a gas containing at least one of hydrogen and carbon monoxide and may, and usually does, contain carbon dioxide.

Overview

The processes and control systems of this invention provide for high anaerobic bioconversion efficiencies of syngas to alcohol. The processes use bioreactors that have a substantially uniform liquid composition and a substantially non-uniform substrate concentration such as deep tank bioreactors and certain electron to carbon ratios and partial pressures of carbon dioxide in the substrate depleted gas phase from the bioreactors to provide the high efficiency of bioconversion.

Syngas Generation

The source of the syngas is not critical to the broad aspects of this invention.

Gasification, partial oxidation, and reforming (autothermal and steam) of biomass or fossil carbonaceous materials can be used. Gasification and partial oxidation processes are disclosed in copending U.S. patent application Ser. No. 13/304,902, filed on Nov. 28, 2011, hereby incorporated by reference in its entirety. Rice, et al, in "Autothermal Reforming of Natural Gas to Synthesis Gas", Reference: KBR Paper #2031, Sandia National Laboratories, April 2007, discuss autothermal reforming and conditions. Steam reforming is a widely practiced commercial unit operation. See Logdberg, et al., "Natural Gas Conversion", Haldor Topsoe publication (undated). Reforming in the presence of carbon dioxide is known as carbon dioxide reforming with the partial pressure of carbon dioxide causing a shift in the product distribution of the reforming. See, for instance, Madsen, et al, "Industrial Aspects of $CO_2$-reforming", Paper No. 28f, presented at the AIChE Spring Meeting, Houston, Tex., March 1997. Reforming is a temperature dependent equilibrium reaction, and thus the addition of hydrogen, carbon monoxide or carbon dioxide will affect the distribution of steam, hydrogen, carbon monoxide and carbon dioxide from the fresh feed although the distribution in the produced syngas will be set by the thermodynamic equilibria.

Where a source of carbon dioxide is available, steam reforming is generally preferred due to the high hydrogen concentration of the produced syngas and the relative absence of contaminants that must be removed to prevent deleterious effects on the microorganisms for the anaerobic bioconversion to alcohol. Additionally, steam reforming, being non-oxidative, provides a syngas that is relatively free of nitrogen which would be present in the syngas produced by a partial oxidation or autothermal reforming process using air or enriched air as the oxygen source. Another advantage of steam reforming is that the depleted gas phase from the bioreactors can be used as a portion of the fuel required for providing the heat for the steam reforming. By using the depleted gas phase to provide heat, and offset of fresh carbonaceous feed occurs and thereby enhances the net conversion of fresh carbonaceous feed to alcohol. The portion of the carbonaceous feed that can be offset will depend upon the volume and heating value of the depleted gas phase.

An advantage of autothermal reforming, as stated above, is that operating conditions can be selected to provide a syngas having the sought electron to carbon atom ratio. The electron to carbon ratio can be adjusted by operational variables for autothermal reforming. For instance, increasing the preheat temperature of the feed to the autothermal reforming enables a reduction in the amount of combustion required during the autothermal reforming to provide the sought temperature. Thus the concentration of carbon dioxide in the syngas is reduced. The steam to hydrocarbonaceous feed ratio can also be adjusted to provide the sought electron to carbon ratio with higher steam ratios increasing the electron to carbon ratio. Since the processes of this invention enable a high conversion of hydrogen to alcohol, advantageous processes can be provided where air or oxygen-enriched air is used as the oxygen source for the autothermal reforming. Although the nitrogen diluent may reduce the energy density of the substrate depleted gas phase from the bioreactor assembly and render it less useful or without utility as a gas for combustion to provide heat, e.g., for a steam boiler, high feedstock to alcohol conversions can still be achieved.

Since the unit operations to make the syngas can vary widely, it is understood that the compositions of the syngas may similarly vary widely including the presence of components other than hydrogen, carbon monoxide and carbon dioxide, which components may be inert such as nitrogen and methane or components that may have to be removed due to potential adverse effects on the microorganisms such as hydrogen cyanide. Processes for removing adverse components include those disclosed in U.S. patent application Ser. No. 13/304,902, filed on Nov. 28, 2011; Ser. No. 13/440,953, filed on Apr. 5, 2012; and Ser. No. 13/525,079, filed on Jun. 15, 2012; and U.S. Pat. No. 7,927,513 filed on Oct. 27, 2009 and U.S. Pat. No. 8,303,849, filed on Nov. 9, 2010, all hereby incorporated by reference in their entireties. Also, the relative ratios among hydrogen, carbon monoxide and carbon dioxide may vary widely. An advantage of the control system of the processes of this invention is that such variations in the relative ratios can be accommodated to provide a substrate gas to the bioreactor assembly that enables achieving a high conversion of hydrogen and carbon monoxide to alcohol.

In some instances, more than one source of syngas may be used, and it may be desired to use different types unit operations, e.g., a steam reformer and an autothermal reformer or partial oxidation unit or gasifier, to produce syngas so as to provide the desired overall substrate gas composition.

Syngas Composition Adjustment

In the processes of this invention, the syngas composition is controlled to provide certain electron to carbon ratios and amounts of carbon dioxide in the substrate gas introduced into the bioreactor assembly. Also, it may be necessary to remove one or more contaminants from the syngas to provide a suitable substrate feed to the bioreactor assembly as discussed above. Due to the dependence of the distribution of hydrogen and carbon oxides on the type or types of syngas producing unit operations used, it may be necessary to adjust the distribution of hydrogen and carbon oxides. Adjustment may be effected by selective removal of one of these components or by the addition of one or more of these components from another source. As noted above, the use of two different syngas producing unit operations may be used to provide a composite syngas having the sought composition.

Selective removal of one of hydrogen, carbon monoxide and carbon dioxide is generally not preferred since it represents a loss of hydrogen or carbon values for the bioconversion and a loss of overall conversion efficiency from the carbonaceous feedstock to alcohol. In some instances, however, the removed component may have more valuable utility that economically justifies its removal to provide the sought syngas composition as opposed to adding a component from an external source. Any suitable unit operation may be used to separate a component from the syngas such as sorption, liquefaction, membrane separation and the like.

Where hydrogen is required to be added, it can be procured from any suitable source. Where steam reforming is used to produce the syngas, a unique opportunity exists to provide a renewable component to alcohol. Steam reforming provides a syngas that requires additional carbon dioxide to be added to meet the electron to carbon and carbon dioxide concentration parameters. Sources of the additional carbon dioxide can be derived directly or indirectly from biomass. One convenient source of relatively high purity carbon dioxide is from ethanol plants bioconverting carbohydrates, including but not limited to sugars and starches, to ethanol or other alkanols and diols. In some instances, between about 20 to 45 or more percent of the alcohol can be composed of carbon from renewable sources where using a methane steam reforming unit operation to produce syngas.

The electron to carbon ratio of the substrate gas after compositional adjustments is in the range of about 5.2:1 to 6.8:1, preferably between about 5.5:1 to 6.5:1, and most preferably between about 5.5:1 to 6.4:1. Table I provides typical compositions of the overall, or cumulative, substrate gas fed to the bioreactor assembly using syngas from steam reforming.

TABLE I

| Component | Minimum | Maximum | Preferred Minimum | Preferred Maximum |
| --- | --- | --- | --- | --- |
| Carbon Monoxide, mole % | 0 | 30 | 10 | 20 |
| Hydrogen, mole % | 50 | 75 | 60 | 70 |
| Carbon Dioxide, mole % | 2.5 | 50 | 10 | 15 |
| Methane, mole % | 0.1 | 30 | 0.3 | 10 |
| Nitrogen, mole % | 0 | 10 | 0 | 5 |
| Ammonia, ppm (mole) | 0.01 | 100 | 0.1 | 75 |
| Hydrogen cyanide, ppm (mole) | 0.001 | 1 | 0.001 | 0.01 |
| Other, ppm (mole) | 0.01 | 100 | 0.01 | 50 |

(Excluding water)

Alcohol, Microorganisms and Fermentation Conditions:

The alcohol or alcohols produced in the processes of this invention will depend upon the microorganism used for the fermentation and the conditions of the fermentation. One or more microorganisms may be used in the fermentation menstruum to produce the sought alcohol. Bioconversions of CO and $H_2/CO_2$ to propanol, butanol, ethanol and other alcohols are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA- 10522 U.S. Pat. No. 8,143,037, filed on Mar. 19, 2010. All of these references are incorporated herein in their entirety.

Suitable microorganisms for bioconversion of syngas to alcohol generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723, hereby incorporated by reference in its entirety, discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and syngas residence time, are preferably sufficient to achieve the sought conversion efficiency of hydrogen and carbon monoxide and will vary depending upon the design of the fermentation reactor and its operation. The pressure may be subatmospheric, atmospheric or super atmospheric, and is usually in the range of from about 90 to 1000 KPa absolute and in some instances higher pressures may be desirable for biofilm fermentation bioreactors. As most bioreactor designs, especially for commercial scale operations, provide for a significant height of aqueous menstruum for the fermentation, the pressure will vary within the fermentation bioreactor based upon the static head.

The fermentation conditions are preferably sufficient to effect at least about 85, preferably at least about 90, percent of the hydrogen in the substrate gas fed to the bioreactor assembly to alcohol. As stated above, a combination of bubble size and duration of contact with the aqueous fermentation menstruum are necessary to achieve these high conversions. However, the ease and ability to achieve these high conversions is also dependent upon having the specified electron to carbon ratios and carbon dioxide partial pressures in the substrate depleted gas phase. For commercial operations, the fermentation operation preferably provides a total molar conversion of hydrogen and carbon monoxide in the substrate gas feed in the range of at least about 93, preferably at least about 97, mole percent. If required to provide adequate contact time between the gas bubbles and the aqueous fermentation menstruum, more than one bioreactor may be used in gas flow series in the bioreactor assembly. The use of sequential, deep tank bubble column bioreactors is disclosed in U.S. patent application Ser. No. 13/243,062, filed on Sep. 23, 2011, herein incorporated by reference in its entirety.

The rate of supply of the gas feed under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important.

Preferably the substrate gas is introduced into the bioreactor in the form of microbubbles. Often the microbubbles have diameters in the range of 0.01 to 0.5, preferably 0.02 to 0.3 millimeter. Preferably the substrate gas is injection using a motive fluid. Variations in the motive liquid flow rate can be used to modulate the microbubble size and thus modulate the rate of transfer of carbon monoxide and hydrogen to the liquid phase. Moreover, the modulation provides microbubbles that provide a stable gas-in-liquid dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The bubble size generated by the injectors will be influenced by, among other factors, the rate of liquid flow through the injector and the ratio of gas phase to liquid phase passing through the injector as well as characteristics of the aqueous menstruum itself including, but not limited to its static liquid depth. See also, U.S. patent application Ser. No. 13/243,062, filed on Sep. 23, 2011. In some instances the microbubbles which form a less dense gas-liquid dispersion and any motive fluid used to generate the microbubbles, can facilitate liquid mixing in a bioreactor.

Bioreactor Assembly

The bioreactor assembly may comprise one or more bioreactors which may be, with respect to gas flow, in parallel or in series flow. The bioreactor assembly contains a bioreactor that is characterized as having a substantially uniform aqueous phase composition and a substantially non-uniform substrate concentration. Where more than one bioreactor is used in gas flow series, at least the terminal bioreactor in the series has this characterization. Representative of these types of bioreactors are bubble column bioreactors, stirred tank bioreactors where the stifling rate is below that which results in a substantially uniform substrate composition (liquid and gas phase) in the bioreactor, and bioreactors having gas-lift riser section or sections.

Because of economy of capital cost and operation, deep tank bioreactors are preferred. Regardless of the type of deep tank bioreactor, especially where using microbubbles that promote a stable dispersion of bubbles in the aqueous menstruum, mixing currents exist that not only assure the relatively uniform aqueous phase composition but also increase the contact time between the gas bubbles and the aqueous menstruum.

The processes of this invention are particularly attractive for deep tank bubble column bioreactors which are less expensive from cost and operating standpoints than other types of deep tank bioreactors. Where bubble column bioreactors are used, the depth of the aqueous fermentation menstruum is often at least about 15, say, between about 20 and 30, preferably between about 20 and 25, meters. The significant depths can be used in the bubble column bioreactors without undue risk of carbon monoxide inhibition as the substrate gas compositions can provide a relatively low partial pressure of carbon monoxide even with these significant depths of aqueous fermentation menstruum while still achieving the sought electron to carbon atom ratio.

Where more than one bioreactor is used in gas flow series, the initial bioreactor may be of any suitable configuration including, but not limited to, bubble column bioreactors; jet loop bioreactors; stirred tank bioreactors; trickle bed bioreactors; biofilm bioreactors; moving bed bioreactors; membrane bioreactors and static mixer bioreactors including, but not limited to, pipe bioreactors.

Substrate Depleted Gas Phase

The substrate depleted gas phase egressing from the aqueous fermentation menstruum will contain a small fraction of the hydrogen and carbon oxides introduced into the bioreactor assembly as the substrate gas. Inerts such as nitrogen and primarily methane will comprise a portion of the depleted gas phase where syngas from steam reforming or oxygen fed autothermal reforming is used. Thus the depleted gas phase has heating value when combusted or can be recycled, at least in part, to the unit operation used for producing the syngas or to a steam boiler or the like. The carbon dioxide content of the substrate depleted gas phase is sufficiently low that it may be recycled as feed to the unit operation used for producing the syngas without unduly affecting the composition of the reformate. Hence, high methane-content substrate depleted gases could be admixed with feedstock to a reformer, especially prior to the sulfur remove unit operation of the reformer. The depleted gas phase may also contain sulfur-containing compounds, alcohol and the like volatilized from the aqueous fermentation menstruum. Table II provides typical concentrations of the major components in the substrate depleted gas phase from the bioreactor assembly using syngas from a steam reformer. The ratio of methane to hydrogen varies depending upon the amount of methane in the syngas, the conversion of hydrogen and whether a methane-containing carbon dioxide gas is used to adjust the electron to carbon ratio. In the aspect of this invention using an air fed autothermal reformer, nitrogen is often the major component of the substrate depleted gas, and sometimes is between about 60 and 90 volume percent of the substrate depleted gas. Due to the high nitrogen content, the substrate depleted gas has no value as a fuel. Accordingly, preferred operations using air fed autothermal reformers comprise using electron to carbon ratios that effect a hydrogen conversion to alcohol of at least about 90, preferably at least about 92, percent.

TABLE II

| Component | Usual, mole percent at 100 kPa absolute | Preferred, mole percent at 100 kPa absolute |
|---|---|---|
| Carbon monoxide | 0 to 5 | 0 to 1.5 |
| Hydrogen | 10 to 90 | 15 to 85 |
| Nitrogen | 0 to 10 | 0 to 2 |
| Methane | 5 to 90 | 5 to 80 |
| Carbon dioxide pp kPa | 2.5 to 20 or 25 kPa | 3.5 to 10 kPa |

(Mole percentages on an anhydrous basis, partial pressure include water vapor. The gas feed may contain other components)

Product Recovery

The fermentation vessel may have added from time to time or continuously one or more streams of water, nutrients or adjuvants, and microorganisms. A portion of the aqueous menstruum is withdrawn from time to time or continuously from the bioreactor for product recovery. Usually, the withdrawal is made at a point at the upper portion of the aqueous menstruum in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679, herein incorporated by reference in its entirety, shows an arrangement for a product recovery bioreactor that recovers an ethanol product from a bioreactor.

Drawings

A general understanding of the invention and its application may be facilitated by reference to the Figures. The Figures are not in limitation of the broad aspects of the invention.

FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other alcohols such as i-butanol, n-butanol, and n-propanol.

For purposes of discussion, natural gas will be used for providing the syngas for use in apparatus 100. It should be recognized that other carbonaceous sources can be used to provide syngas. The primary conversion process depicted is steam reforming although other syngas producing conversion unit operations can be used such as gasification, partial oxidation and autothermal reforming. Natural gas is supplied via line 102 and passed to pretreatment assembly 104. Pretreatment assembly 104 typically is adapted to remove sulfur compounds from the natural gas. In some instances, pretreatment assembly 104 is encompassed within a steam reforming unit operation.

The natural gas having its sulfur content reduced is passed via line 106 to heat exchanger 108 and then to steam reformer 110. Steam reformer 110 converts the hydrocarbons in the natural gas to a syngas containing hydrogen, carbon monoxide and carbon dioxide. Lower pressure operations of steam reformer 110 provide less methane breakthrough then at higher pressure operations. Accordingly, for purposes of discussion, a lower pressure steam reforming unit operation is used, and the syngas contains about 75 mole percent hydrogen, about 18 mole percent carbon monoxide, about 5.5 mole percent carbon dioxide, and about 1.5 mole percent methane on and anhydrous basis.

The steam reforming is highly endothermic and hotbox 112 is provided to supply heat for the steam reforming. Syngas exits steam reformer 110 via line 114 which directs the syngas to heat exchanger 108 to preheat the incoming natural gas to steam reformer 110. After passing through heat exchanger 108, carbon dioxide is supplied to the syngas in line 114 via line 116 in an amount sufficient to adjust the electron to carbon ratio of the syngas to about 6.3:1 and provide the sought amount of carbon dioxide in the depleted gas phase (off gas) from the bioreactor assembly. As shown, the combined syngas and carbon dioxide stream is subjected to treatment in syngas purification unit 118. The function of syngas purification unit 118 will depend upon the source of the syngas and carbon dioxide and serves to remove components that may be adverse to the microorganisms used for the anaerobic fermentation of the syngas to ethanol such as hydrogen cyanide, ethylene, and acetylene. Syngas purification unit 118 is optional, and thus using syngas from a steam reformer and carbon dioxide from an ethanol plant, it is not essential for the process depicted in the Figure.

The combined syngas and carbon dioxide stream (substrate gas) is passed from syngas purification unit 118 to bioreactor assembly 122 via line 120. For purposes of discussion, bioreactor assembly 122 comprises a plurality of deep tank bubble column bioreactors, one of which is shown in the drawing. Each deep tank bioreactor contains an aqueous fermentation menstruum having a depth of about 20 meters. The substrate gas is introduced at the bottom of the bioreactor in the form of finely dispersed microbubbles, e.g., using a slot eductor. The duration of the microbubbles in the bioreactor is sufficient to bioconvert at least 90 percent of the hydrogen and at least 98 percent of the carbon monoxide to ethanol.

Aqueous fermentation menstruum is continuously withdrawn from bioreactor assembly 122 via line 124. The withdrawn fluid is passed to a product recovery assembly generally designated by 126. Product recovery assembly 126 comprises a number of unit operations to remove solids, entrained gases and recover ethanol. Usually product recovery assembly 126 contains a distillation assembly to fractionate the withdrawn fluid into an ethanol product stream which is removed via line 128 and a water fraction which is removed via line 132. Centrifuges or other solid-liquid separation unit operations may be used to remove cells and other solid debris from the fluid prior to it being passed to the distillation assembly, or the fluid may be passed to the distillation assembly without the removal of solids with the solids being removed with the still bottoms. As shown, a solids-containing stream is removed from product recovery assembly 126 via line 134. The solids-containing stream may be directed to digesters to recover carbon and nutrient values. The withdrawn fluid will also typically include lower boiling components such as methane and hydrogen. These lower boiling components are shown as being removed from a product recovery assembly 126 via line 130. Due to the high efficiency of the processes of this invention, often the lower boiling components have a lower heating value and are sent to a flare for disposal.

Returning to a bioreactor assembly 122, make-up water to replenish aqueous menstruum removed for product recovery is provided via line 121. The make-up water may contain nutrients and other adjuvants for the anaerobic fermentation, and may also contain microorganisms for the bioconversion. Substrate depleted gas phase is emitted from the top of the aqueous fermentation menstruum in bubble column bioreactor 122. The depleted gas phase contains about 3 volume percent carbon dioxide at substantially atmospheric pressure. The depleted gas phase is withdrawn from bioreactor assembly 122 via line 136. The depleted gas phase contains methane, hydrogen, carbon dioxide, and relatively little carbon monoxide and thus has value either as a supplement to the natural gas forced steam reforming or as a fuel for the steam reformer. As shown, the depleted gas phase in line 136 can be passed via line 138 to line 102 and then passed to pretreatment assembly 104. Since the depleted gas phase is derived from contact with the aqueous fermentation menstruum, it can contain sulfur compounds that were present in the aqueous menstruum as adjuvants for the microorganisms. The pretreatment assembly 104 serve to remove these sulfur compounds to provide a gas feed suitable for the catalytic steam reforming. In addition, or alternatively, depleted gas phase may be passed via line 140 to line 142 to supply natural gas to hotbox 112 for steam reformer 110. As shown, line 142 obtains the natural gas for hotbox 112 from line 102.

Carbon dioxide to provide the desired electron to carbon ratio for the substrate gas is obtained from an ethanol plant as described above. Other sources of carbon dioxide can be used. FIG. 1 illustrates that natural gas can be passed via line 144 to partial oxidation unit 146. Partial oxidation unit 146 serves to partially oxidize the methane with oxygen, preferably substantially pure oxygen or oxygen enriched air, at elevated temperature to generate a gas containing carbon dioxide, carbon monoxide and hydrogen. Considerable flexibility exists in the operation of partial oxidation unit 146 to provide a desired mole ratio of carbon dioxide to hydrogen such that when combined with the syngas from steam reformer 110, the substrate gas has the desired electron to carbon ratio and carbon dioxide content. Partially oxidize gases exit partial oxidation unit 146 via line 148. Not shown, but often desirable, is using the partially oxidized gases which are at a high temperature as a source of heat for indirect heat exchange with the natural gas being provided to steam reformer 110. The partially oxidized gases are directed to line 116 where they are directed for combination with the syngas from steam reformer 110 in line 114. Due to the high temperature of the partial oxidation syngas purification unit 118 is typically used. The partially oxidize gases can contain aromatic, ethylenic, acetylenic and hydrogen cyanide components that are preferably removed prior to introducing the substrate gas into bioreactor assembly 122.

In another embodiment illustrated by FIG. 1, all feedstock in line 102 is passed via lines 142 and 144 to autothermal reformer 146. Line 147 provides the oxygen for the autothermal reforming. The oxygen may be sourced from an oxygen plant and thus be relatively high purity, from air or from oxygen enriched air produced by admixing air with purer forms of oxygen or by partial separation of nitrogen from air, e.g., by membrane separation or swing sorption. In this embodiment, the syngas may have a suitable electron to carbon atom ratio for introducing into bioreactor assembly 122 after suitable removal of deleterious components.

Modeling

For purposes of illustration and not in limitation of the invention, processes for fermentation have been modeled using different substrate gas compositions. The models are for the use of a bubble column having a diameter of about 23 meters to produce about 63,400 liters per hour of ethanol. The gas flow to the bioreactor is varied to maintain the same ethanol production rate. The details are provided in Table III.

TABLE III

| | Case A | Case B (Comp) | Case C (Comp) |
|---|---|---|---|
| Substrate composition fed, mole %: | | | |
| Hydrogen | 70 | 72 | 74 |
| Carbon monoxide | 17 | 18 | 18 |
| Carbon dioxide | 10 | 7.5 | 5.5 |
| Water | 0.65 | 0.67 | 0.68 |
| Nitrogen | 0.04 | 0.05 | 0.05 |
| Methane | 1.6 | 1.6 | 1.7 |
| $e^-/C$ of substrate composition | 6.35 | 7.16 | 7.83 |
| Ratio of quiescent height of aqueous menstruum to that of Case C to obtain same ethanol productivity | 1.3:1 | 1.1:1 | 1:1 |
| Conversion, % | | | |
| Hydrogen | 90 | 75 | 63 |
| Carbon monoxide | 99 | 97 | 95 |
| pp of carbon dioxide in off gas, kPa | 3.4 | 3.6 | 3.8 |

In Case B, the quiescent height of the aqueous menstruum could be increased but substantially no increase in hydrogen conversion would be obtained.

The preamble to any claim in this invention is part of the entire claim and applies to interpreting the scope and coverage of each claim.

It is claimed:

1. A continuous process for the anaerobic bioconversion of a gas substrate comprising carbon monoxide, hydrogen and carbon dioxide in an aqueous menstruum containing microorganisms suitable for converting said substrate to alcohol comprising:

a. continuously introducing said substrate in the form of gas bubbles at one or more gas inlets of a bioreactor assembly having at least one bioreactor for containing said menstruum, said bioreactor having at least one gas inlet and at least one gas outlet and at least one bioreactor in the bioreactor assembly is characterized as having a substantially uniform aqueous menstruum and a substantially non-uniform substrate between the gas inlet and the gas outlet wherein the cumulative substrate introduced into the bioreactor assembly through said one or more gas inlets has a ratio of electrons to carbon atoms in the range of 5.2:1 to 6.8:1;

b. maintaining contact between the gas bubbles and said menstruum to provide an alcohol-containing menstruum and a substrate depleted gas phase at a gas outlet of said bioreactor assembly, said duration of contact being sufficient to convert at least 80 percent of the hydrogen in the gas substrate to alcohol;

c. continuously withdrawing substrate depleted gas phase from said bioreactor assembly at said at least one gas outlet wherein the substrate depleted gas phase being withdrawn from the bioreactor assembly has a partial pressure of carbon dioxide in the range of 2.5 and 25 kPa; and d. continuously or intermittently withdrawing a portion of said menstruum from said bioreactor assembly for recovery of said alcohol, said withdrawal being sufficient to maintain the alcohol in said menstruum below a concentration that unduly adversely affects the microorganisms.

2. The process of claim 1 wherein the ratio of electrons to carbon in the gas substrate is between about 5.5:1 to 6.5:1.

3. The process of claim 2 wherein the partial pressure of carbon dioxide in the depleted gas is between about 3.5 and 10 kPa.

4. The process of claim 1 wherein the bioreactor assembly comprises at least two bioreactors in gas flow sequence.

5. The process of claim 4 wherein at least the last bioreactor in gas flow sequence is characterized as having a substantially uniform aqueous menstruum and a substantially non-uniform substrate.

6. The process of claim 1 wherein the gas substrate comprises syngas from a steam reformer and contains at least about 80 mole percent carbon monoxide, hydrogen and carbon dioxide.

7. The process of claim 6 wherein the bioreactor assembly comprises a deep tank bioreactor.

8. The process of claim 1 wherein the gas substrate is generated reforming a carbonaceous feedstock.

9. The process of claim 8 wherein the reforming comprises autothermal reforming and the operation of the autothermal reforming provides a syngas having an electron to carbon ratio of between about 5.7:1 to 6.0:1.

10. The process of claim 8 wherein the reforming comprises steam reforming and the cumulative gas substrate has an electron to carbon atom ratio of between about 5.8:1 to 6.4:1.

11. The process of claim 10 wherein the steam reforming provides a reformate having an electron to carbon ratio greater than 8:1 and carbon dioxide is added to bioreactor assembly to provide a cumulative gas substrate having an electron to carbon atom ratio of between about 5.8:1 to 6.4:1.

12. The process of claim 11 wherein (a) sufficient duration of contact of the gas bubbles with the aqueous menstruum in the reactor assembly is provided, (b) the electron to carbon ratio is maintained in the range of 5.5:1 to 6.8:1, (c) the partial pressure of carbon dioxide in the depleted gas phase is between about 3.5 and 10 kPa and (d) carbon monoxide, hydrogen and carbon dioxide comprise at least about 80 mole percent of the gas substrate, such that energy efficiency based on feedstock to the steam reformer as feedstock and fuel is at least about 60 percent.

13. The process of claim 12 wherein the bioreactor assembly comprises a deep tank bioreactor.

14. The process of claim 13 wherein the deep tank bioreactor is a bubble column bioreactor.

15. The process of claim 14 wherein the energy efficiency based on carbon fed to the steam reformer as feedstock and fuel is at least about 65 percent.

16. The process of claim 1 wherein concentration of the alcohol is within 0.2 mole percentage points in the substantially uniform aqueous menstruum between the gas inlet and the gas outlet.

17. The process of claim 1 wherein concentration of at least one of the carbon monoxide, the hydrogen, and the carbon dioxide of the substantially non-uniform substrate changes by at least 50 percent between the gas inlet and the gas outlet.

* * * * *